United States Patent [19]
Nosov

[11] Patent Number: 5,869,973
[45] Date of Patent: Feb. 9, 1999

[54] TIME-DOMAIN DIELECTRIC SPECTROSCOPY METHOD AND APPARATUS

[76] Inventor: Eugene I. Nosov, 4746 S. 83rd St., Apt. 20, Omaha, Nebr. 68127

[21] Appl. No.: 783,969

[22] Filed: Jan. 15, 1997

Related U.S. Application Data

[63] Continuation-in-part of Ser. No. 590,687, Oct. 26, 1995, abandoned.

[51] Int. Cl.[6] ............................. G01N 27/22; G01R 27/26
[52] U.S. Cl. ......................... 324/678; 324/663; 324/664
[58] Field of Search ................................... 324/439, 663, 324/664, 665, 671, 672, 678, 679, 686; 73/61.44, 61.43

[56] References Cited

U.S. PATENT DOCUMENTS

| | | | |
|---|---|---|---|
| 3,753,092 | 8/1973 | Ludlow et al. | 324/672 X |
| 3,784,905 | 1/1974 | Blackwell | 324/663 |
| 4,429,272 | 1/1984 | Bungay | 324/663 |
| 4,433,286 | 2/1984 | Capots et al. | 324/663 |
| 4,777,431 | 10/1988 | Day et al. | 324/663 X |
| 5,394,097 | 2/1995 | Bechtel et al. | 324/663 X |
| 5,461,321 | 10/1995 | Sanders et al. | 324/678 |

OTHER PUBLICATIONS

Waldmeyer et al., "A Simple Technique in Dielectric Time–Domain Spectroscopy," J. Phys. D: Appl. Phys., vol. 8, pp. 1513–19 (1975). (month unavailable).

Hart et al., "Time–Domain Spectroscopy of Apples," IEEE transactions on Electrical Insulation, vol. 24(4), pp. 627–34 (1989). (Month unavailable).

Voss et al., "Time Domain Spectroscopy (TDS) of Dielectric Properties up to 15 GHz with Voltage Pulses. Application to Solids and Liquids," J. Phys. E: Sci. Instrum., vol. 17, pp. 981–983 (1984). (month unavailable).

Frame et al., "Observations on Time Domain Dielectric Spectroscopy," J. Phys. D: Appl. Phys., vol. 18, pp. L99–L102 (1985). (month unavailable).

Feldman et al., "Time Domain Dielectric Spectroscopy. A New Effective Tool for Physical Chemistry Investigation," Colloid and Polymer Science, vol. 270, pp. 768–780 (1992). (Month unavailable).

Skodvin et al., "Water–in–Crude Oil Emulsions from the Norwegian Continental Shelf IX.," J. Colloid and Interface Science, vol. 166, pp. 43–50 (1994). (month unavailable).

Kaatze et al., "Dielectric Relaxation Spectroscopy of Liquids: Frequency Domain and Time Domain Experimental Methods,"J. Phys. E: Sci. Instrum., vol. 13, pp. 133–141 (1980). (month unavailable).

Jonscher, The "Universal" Dielectric Response: Part I, IEEE Electrical Insulation Magazine, vol. 6, No. 2, pp. 16–21 (1990). (month unavailable).

Jonscher, The "Universal" Dielectric Response: Part II, IEEE Electrical Insulation Magazine, vol. 6, No. 3, pp. 24–27 (1990). (Month unavailable).

Jonscher, The "Universal" Dielectric Response: Part III, IEEE Electrical Insulation Magazine, vol. 6, No. 4, pp. 19–24 (1990). (month unavailable).

Cole, "Time–Domain Spectroscopy of Dielectric Materials," IEEE Transactions on Instrumentation and Measurement, vol. IM–25, No. 4, pp. 371–375 (1976). (Month unavailable).

Romanychev et al., "Analysis of Error Sources in Time–Domain Dielectric Spectroscopy," Izmeritel'naya Teknika, No. 8, pp. 61–63 (1992) (English Translation). (month unavailable).

(List continued on next page.)

*Primary Examiner*—Diep N. Do
*Attorney, Agent, or Firm*—Suiter & Associates PC

[57] ABSTRACT

A time-domain dielectric spectroscopy device and method are described wherein measurements are taken of the absorption and dielectric response function of a dielectric material in order to identify dielectric materials.

27 Claims, 14 Drawing Sheets

OTHER PUBLICATIONS

Baba et al., "Measurement of the Dielectric Relaxation of Liquids by Lumped–Capacitor Time–Domain Spectroscopy," Japanese Journal of Applied Physics, vol. 26(3), pp. 479–481 (1987). (month unavailable).

Feldman et al., "Dielectric Relaxation Phenomena Study by the Time Domain Dielectric Spectroscopy," PMSE, Abstract 153. (undated).

Moorhead, Calculation of Dielectric Parameters from Time Domain Spectroscopy Data, Small Perturbations Extended Abstracts, pp. 256–257. (undated).

Hasse et al., "Dielektrische Spektroskopie an Mikro–Emulsionen mittels Zeibereich–Methode," Rapport de la réunion d'automne de la Sociéte Suisse de physique, vol. 54, p. 615, (1981). (month unavailable).

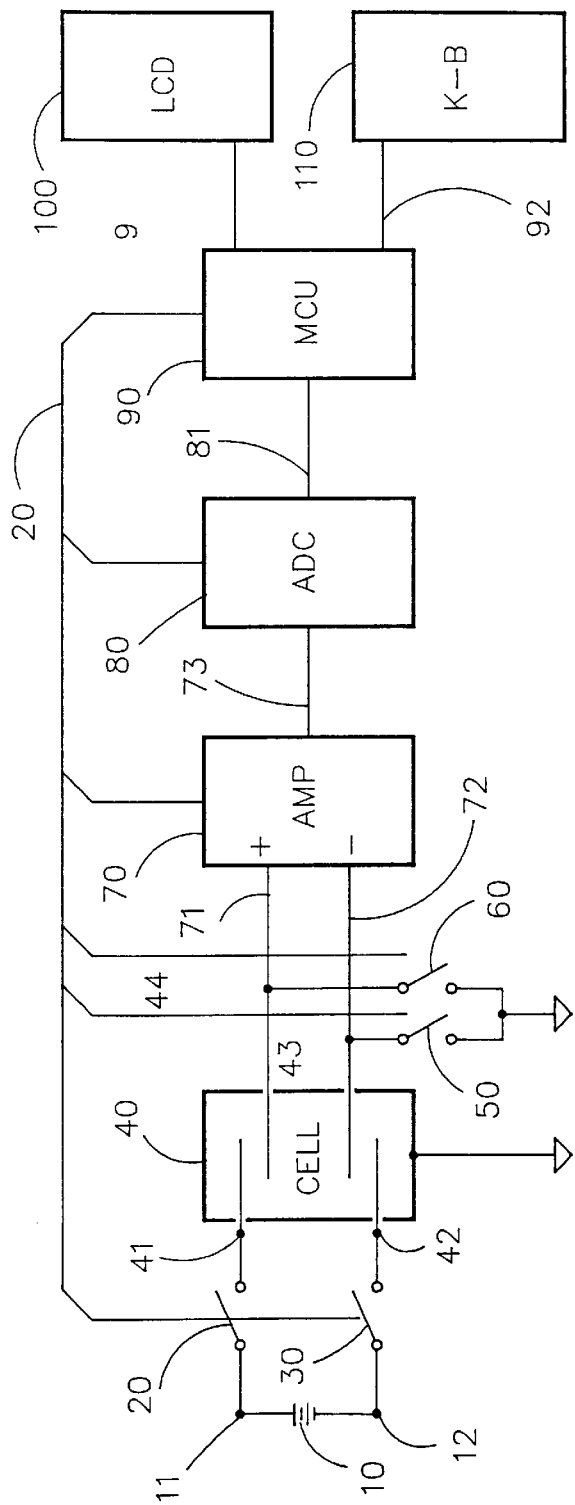
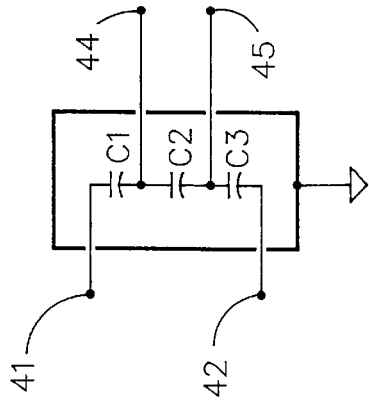
FIG. 4
FIG. 5

TIME-DOMAIN DIELECTRIC SPECTROSCOPY METHOD AND APPARATUS

CROSS REFERENCE TO RELATED APPLICATION

The present application is a continuation-in-part of prior U.S. patent application Ser. No. 08/590,687 filed on Oct. 26, 1995, now abandoned.

TECHNICAL FIELD

The present invention relates to dielectric spectroscopy and more particularly to time-domain dielectric spectroscopy.

BACKGROUND OF THE INVENTION

Dielectric spectroscopy (DS) is one of several methods used for physical and chemical analysis of materials. Most advanced among the methods are chromatographic, spectroscopic, mass-spectrometric, thermodynamic and electric. All of the foregoing methods are characterized by high precision and accuracy with the exception of thermodynamic and electric which are of relatively low accuracy. Electric methods are able to identify the basic characteristics of a substance, such as $tg\sigma$ and $\epsilon$. However, the dielectrics of different classes may share identical values for $tg\sigma$ and $\epsilon$, making it impossible to identify a substance based on these parameters alone.

Although DS has been under continued development it does not currently enjoy substantial or significant use since it requires a great deal of complex and expensive equipment operated by highly skilled technicians. Additionally, information on dielectric materials could only be obtained over limited frequency ranges.

Known to the art are several time-domain spectroscopy (TDS) methods. For example, Waldmeyer and Zschokke-Granacher disclose a single reflection time-domain reflectometry method (J.Phys.D:Appl.Phys. 8:1513–1519, 1975). This method may be utilized to obtain the frequency spectrum of the permittivity of materials. In practice, the voltage step pulse of a step generator is propagated along a coaxial transmission line where it is at least partially reflected by the test material. The permittivity of the material is determined from the following expression:

$$\epsilon^*(s) = [(2V_o/s)U_s(s) - 1]^2$$

where $V_o/s$ represents the ideal step function of voltage and $U_s(s)$ is the falling and reflecting pulse of the voltage. Another method by Kaatze and Giese (J.Phys.E:Sci.Instrum. 13:133–141, 1980) relies on observations of a sample's response to exciting step voltage pulses. In some basic aspects this method resembles the Fourier Transform technique. Voss and Happ (Phys.D:App.Phys. 17:981–983, 1984) describe a method which uses voltage pulses and allows separation of the test signal from the response in time. The dielectric function g(T) of solids and liquids can be determined from the reflection response. Frame and Fouracre (Phys.D:Appl.Phys. 18:99–102, 1985) use exponential and $t^{-n}$ power law response. The decay current as a function of time is generally found to be of the form:

$$I(t) = Kt^{-n}$$

where K and n are constants, that is the dielectric response function of the form:

$$f(t) = Kt^{-n}/C_oV_o$$

where $C_o$ is the capacitance of the sample and $V_o$ is the applied voltage. The complex susceptibility as a function of frequency is:

$$X^*(\omega) = K/C_oV_o \int_0^\infty t^{-n} \exp(-j\omega t)dt.$$

Baba and Fujimura (Jap.Journ.App.Phys. 26(3)479–481, 1987) used reflected waves from the surface of the dielectric under test and obtained relaxation parameters of dielectric $\epsilon_o$; $\epsilon_\infty$; $t_o$ with the Fourier transform technique. In the method of Hart and Coleman (IEEE Transactions on Electrical Insulation 24(4)627–634, August 1989), a voltage pulse of known shape is applied to the object and the resulting current form measured. Fourier transformation of the time variation of the object's conductance yields the dielectric spectrum. Feldman et al. (Colloid Polym. Sci 270:768–780, 1992) considered the TDS method to be based on the reflectometry principle in time-domain in order to study heterogeneities in the coaxial lines according to the change of the test signal shape. Until the line is homogeneous this pulse is not changed; when heterogeneity is introduced, for example by the presence of a dielectric, the signal is partly reflected from the air-dielectric interface, while the remainder of the signal passes through it. Skodovin et al (J Colloid Interface Sci 166:43–50, 1994) introduced a method of total reflection in which the sample cell is placed at the open end of a coaxial line. The shapes of reflected step pulses from a cell filled with a sample and from a cell filled with a reference liquid were recorded. Via a Fourier transform, the dielectric spectrum of the sample is given by:

$$\epsilon^*(\omega) = \epsilon'(\omega) - i\epsilon''(\omega) - i\sigma/\omega\epsilon_o.$$

All of the reviewed methods of the time-domain dielectric spectroscopy are different from the proposed method. They use a reflection time-domain method for observation of the response of the dielectric sample to exciting step voltage pulses of picoseconds duration.

The positive charge center in an atom of the substance is displaced in relation to the negative charge center when an electric field is placed across an atom as shown in FIG. 1. This is known as polarization. From Frohlich H. (1958) "Theory of Dielectrics" the linear approximation of the dielectric polarization $\bar{P}$ (electric dipole movement of the volume unit) is proportional to the electric field tension $\bar{E}$ in the sample:

(1) $\bar{P} = \chi \bar{E}$ where proportional coefficient $\chi$ is called the dielectric susceptibility.

When an external electric field is applied the dielectric polarization reaches its equilibrium value, not instantly, but over a period of time. By analogy, when the electric field is broken suddenly, the polarization decay caused by thermal motion follows the same law as the relaxation or decay function:

(2) $\alpha(t) = \bar{P}(t)/\bar{P}(o)$.

The value of the displacement vector $\bar{D}$ (t) in the electric field $\bar{E}$ (t) may be written:

$$\bar{D}(t) = \epsilon_\infty \bar{E}(t) + \int_{-\infty}^{t} \bar{E}(t')\phi(t-t')dt' \quad (3)$$

where $\epsilon_\infty$ is the high frequency limit of complex dielectric permittivity $\epsilon^*(\omega)$; $\Phi(t-t')$ is the dielectric response function.

The dielectric response function is:

$$\Phi(t) = \epsilon_\infty + F(t) \quad (4)$$

where $F(t) = (\epsilon_s - \epsilon_\infty)[1-\alpha(t)]$, $\epsilon_s$ is the static dielectric permittivity.

The dielectric response function may be written as follows:

$$\Phi(t) = \epsilon_\infty + (\epsilon_s - \epsilon_\infty)[1-\alpha(t)]. \quad (5)$$

The complex dielectric permittivity $\epsilon^*(\omega)$ is an analog of the dielectric response function in the time-domain:

$$\epsilon^*(\omega) = i\omega L[\phi(t)] = i\omega \int_0^\infty \phi(t)\exp(-i\omega t)dt \quad (6)$$

where L is the operator of the Fourier-Laplace transform.

If the relaxation function is:

$$\alpha(t) \cong \exp(-t/\tau_m) \quad (7)$$

where $\tau_m$ represents the dielectric relaxation time, then the relation first obtained by Debye is true for the frequency domain:

$$[\epsilon^*(\omega) - \epsilon_\infty]/(\epsilon_s - \epsilon_\infty) = 1/(1+i\omega\tau_m). \quad (8)$$

For most of the investigated dielectrics experimental results cannot as a rule, be described by such a relation. This relation is true only for ideal or close to ideal real dielectrics.

The spectral function of the complex dielectric permittivity $\epsilon^*(\omega)$ can be substituted by the dielectric response function in time-domain. This means that time-domain response function of the dielectric, i.e. the current under step-function field, is derived by the Fourier transform from the frequency domain function. These functions are exponential, and may be presented as follows:

$$\omega^{n-1} \leftrightarrows t^{-n} \quad (9)$$

$$\omega^m \leftrightarrows t^{-(m+1)}$$

where $\omega$ is frequency, t is time, n and m are constants, $\leftrightarrows$ is direct and inverse Fourier transform.

This is the mathematical basis for substitution of complex dielectric permittivity $\epsilon^*(\omega)$ in frequency-domain, with the dielectric response function $\Phi(t)$ in time-domain.

As shown in Jonscher AK "Dielectric Relaxation in Solids", the dielectric relaxation process is accompanied by decay current i(t) which is proportional to the dielectric response function:

$$i(t) \propto \Phi(t). \quad (10)$$

Furthermore in Jonscher AK "Dielectric Relaxation in Solids" the universal dielectric response function is:

$$i(t) = \begin{Bmatrix} K_1 & t^{-n} \\ K_2 & t^{-(m+1)} \end{Bmatrix} \quad (11)$$

where $K_1$; $K_2$; n; m are constants, that characterize the microscopic properties of the dielectric. A graph of the decay current is presented in FIG. 2.

In order to get the most complete characteristics of the dielectric, the absorption phenomena will be used. The absorption phenomena is a self-relaxation process after a quick discharge of the dielectric. The absorption phenomena may be described by the following approximate expression:

$$V_a(t) = a\, t^b\, e^{ct} \quad (12)$$

Where t is time, a, b, c, are absorption parameters, and a>0; 0>b>1; c<0; e=2.718. The apparatus presented in this invention goes through the series of steps (OA, AB, BC, CO) to arrive at the absorption curve DEFI. (FIG. 3)

The dielectric is charged on OA interval up to $V_{CH}$ volts, then on AB interval, the dielectric is kept under the same voltage, ($V_{CH}$). Next the dielectric is discharged on BC interval until 0 volts is achieved. At last, the dielectric is kept at 0 volts on CD interval. DEFI interval is an actual absorption phenomenon. The FI interval is the dielectric response function course. The proposed apparatus forms this curve, and also calculates a unique set of a, b, c, m, and n parameters for the dielectric under measurement.

PROPHETIC EXAMPLES

A persistent problem in fuel marketing is the practice among dishonest wholesale and retail vendors of diluting gasoline or diesel fuel with water, or representing fuels to be of higher octane or of different composition than is actually the case. A vendor wishing to assure a high-quality product engages an exemplary embodiment of a TDS device of the present invention which fits between the supplier's fuel dispenser and the mouth of vendor's underground tank. As fuel is being introduced through the dispenser the TDS device calculates the dielectric characteristics of the fuel. Fuel which does not conform with specifications may then be refused. Such a device also reduces the possibility of inadvertent introduction of one type of fuel into a tank intended for another type of fuel. A consumer wishing to assure a high-quality product engages a TDS device which either fits between the dispenser nozzle and the mouth of the vehicle's fuel tank, or is permanently mounted on the vehicle with a remote display within the vehicle. This low-cost device gives a rapid reading of the octane level of the fuel being pumped. If the octane is not as represented, the purchaser disengages and purchases fuel elsewhere.

Laboratory supply companies are expected to deliver precise molar concentrations of highly purified laboratory chemicals. Drug manufacturers likewise are held to high levels of precision and purity in drug formulation. A TDS device of the present invention may be employed to assure samples do not fall outside accepted levels of concentration and can readily identify the presence of impurities.

Paints have a relatively limited shelf life due to changes in chemical composition over time. Exposure to extreme temperatures can speed this process. A TDS profile obtained on a can of paint will determine whether the material meets specifications before it is applied.

Medical applications of TDS sampling include urinalysis and serum analysis, e.g. in the rapid and accurate detection of sugar and insulin levels for diabetics.

The purity of drinking water is of constant concern. TDS evaluation will allow identification of significant levels of impurities and can be programmed to reveal the presence of specific contaminants such as lead.

Conversely, the value of fine crystal is gauged in part on the basis of lead content. A TDS profile on a sample of glassware will reveal whether the lead content is as high as represented, with no harm to the sampled article.

Virtually all legitimate credit cards are produced by a single entity which employs a distinctive plastic in the manufacture of the cards. This plastic has a unique dielectric profile. A vendor wishing to verify the legitimacy of a credit card may employ a TDS device which scans credit cards before a purchase is registered. Forged cards will not conform with the expected dielectric profile and can be refused.

Soil samples can be assayed with TDS to determine the presence of trace minerals for mining applications, as well as to determine the presence of specific contaminants for detoxification efforts.

The efficacy of insulating devices and materials can be assayed with TDS.

The quality of capacitors, transformers, generators and electromotors can be measured against the performance of a TDS counterpart.

Gaseous applications of TDS sampling include emission monitoring in industrial stacks and vehicles.

SUMMARY OF THE INVENTION

Therefore, it is an object of the present invention to provide a novel method and device for time-domain dielectric spectroscopy.

Another object is to provide an electric method of TDS which is highly accurate and precise.

Another object is to make use of the unique polarization characteristics of subject materials to identify said materials.

Yet another object is to provide a method of TDS wherein dielectric response function is measured after charging/discharging of the dielectric sample, absorption phenomena are assessed, and the resulting qualities are compared with known values to identify a sample.

A further object is to provide a compact and portable method and device for TDS.

Still another object is to provide an inexpensive method and device for TDS which requires little technical skill to operate.

These and other features, aspects, and advantages of the present invention will become better understood with regard to the following description, appended claims, and accompanying drawings.

BRIEF DESCRIPTION OF THE DRAWINGS

FIG. 4 is a block scheme of an exemplary apparatus of the instant invention;

FIG. 5 is a block scheme of a sample cell of an exemplary apparatus of FIG. 4;

DETAILED DESCRIPTION OF THE INVENTION

Figure 1:
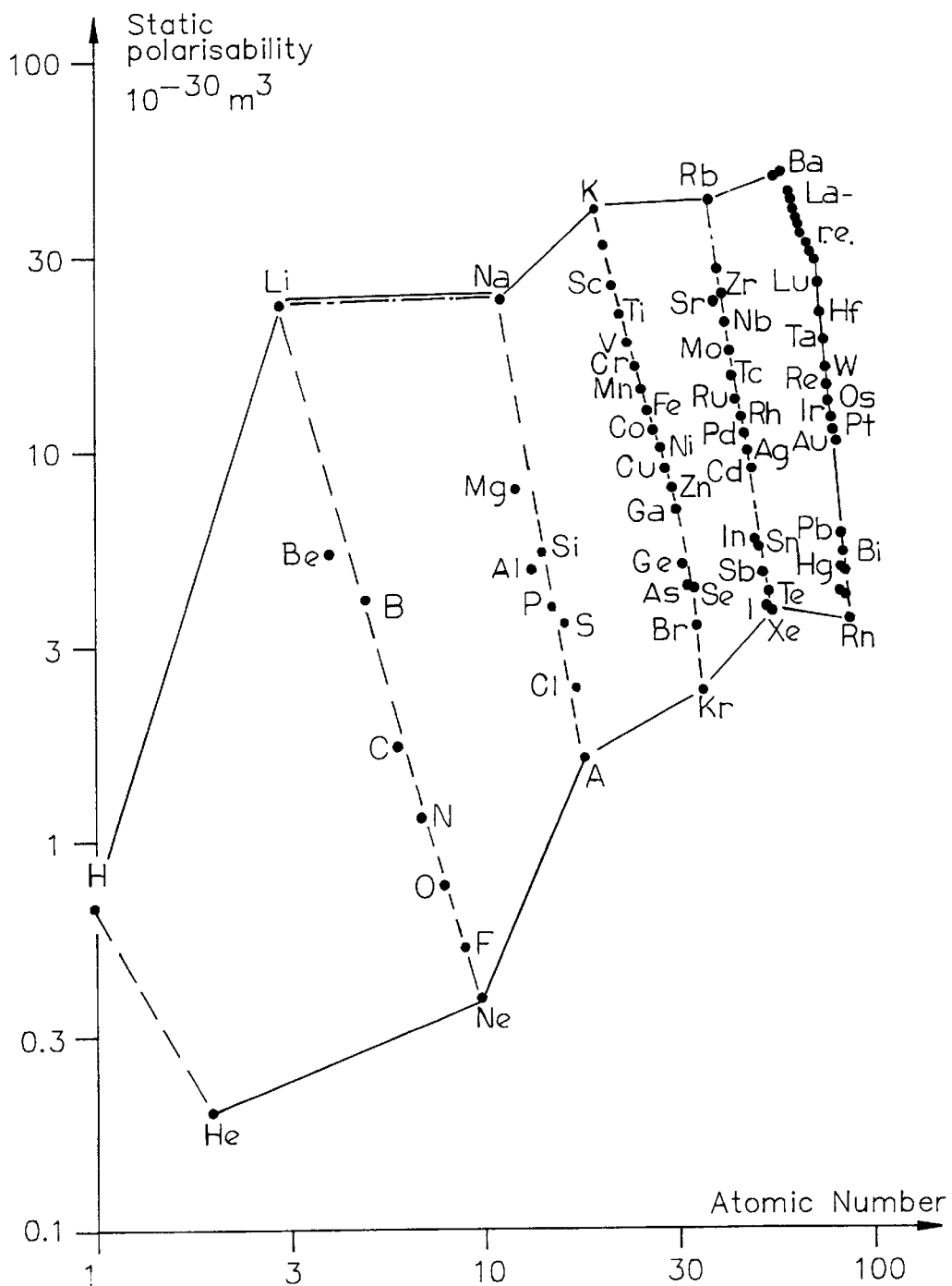
FIG. 1 depicts the logarithm of the static atomic polarization of a number of elements, illustrating the unique position of each element.
Figure 2:
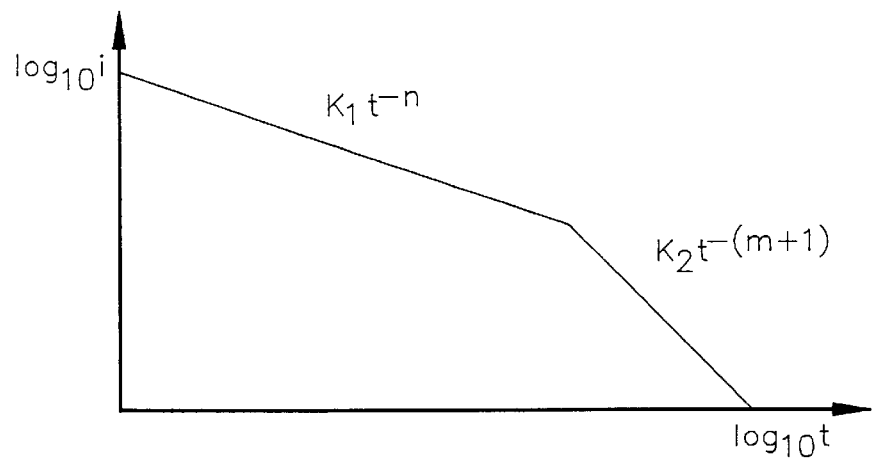
FIG. 2 demonstrates the logarithmic analysis of an exemplary analyte by the instant invention.

A block diagram of the device is presented in FIG. 4. The device consists of a constant voltage source 10, which is connected by a first terminal 11 through normally open (N.O.) switch 20 to the input terminal 41 of the sample cell 40. A second terminal 12 is connected through N.O. switch 30 to the other input terminal 42 of the sample cell 40. The shield of the sample cell 40 is grounded.

The output terminal 43 of the sample cell 40 is connected through N.O. switch 50 to the ground, and at the same time to the input terminal 72 of the low-noise amplifier 70.

The output terminal 44 of the sample cell 40 is connected through N.O. switch 60 to the ground, and at the same time to the input terminal 71 of the low-noise amplifier 70.

The output 73 of the low-noise amplifier 70 is connected to the input of analog to digital converter (ADC) 80. An output (81) of ADC 80 is connected to the input of microcontroller unit (MCU) 90. Display 100 and keyboard 110 are connected to the first 91 and second 92 outputs of MCU 90, respectively.

Switches 20, 30, amplifier 70, and ADC 80 are controlled by MCU 90 through the control bus 120.

The sample cell 40 consists of four electroconductive surfaces. The one pair of these surfaces forms external electrodes which have input terminals 41 and 42, the other pair form internal electrodes which have output terminals 43 and 49.

The equivalent electric scheme of the sample cell is presented in FIG. 5. The capacitors C1, C2, C3 are equal. The total value of these capacitors are chosen for gasoline measurement near 100 pF.

All of these electrodes are enclosed into metallic box which serves as a shield. The measured substance is placed between these four electrodes. The four electrodes design helps to eliminate the harmful polarization of the internal electrodes.

Figure 3:
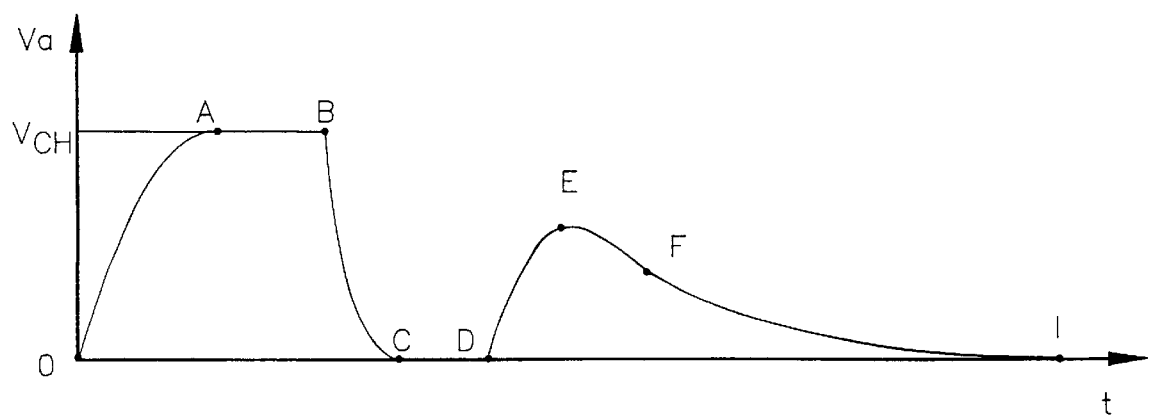
FIG. 3 is a charge and absorption curve of an exemplary analyte by the instant invention.

The device works in several phases. The first phase is forming of the absorption curve on the sample cell 40. At this phase amplifier 70 is set at a gain which equals 1. Switches 20 and 30 are closed for 100 ms. As a result, the device forms charge intervals OA and AB (FIG. 3) after switches 20 and 30 are opened. Switches 50 and 60 are closed for 5–10 ms. Thus BC and CD intervals are formed. Finally switches 50 and 60 are opened, and the absorption curve DEFI (FIG. 3) begins to form. The evidence of this registers on terminals 43 and 44 in the form of an electrical signal. This analog signal is inputted to amplifier 70 through inputs 71 and 72. After the initial amplification, the analog signal is transmitted to ADC 80 through 73. The analog signal is converted into digital code in ADC 80. ADC 80 samples absorption voltage discretely every $t_s$ (sample time interval) FIG. 6. MCU 90 finds the maximum of the absorption voltage from the samples received from ADC 80, and sets the gain on amplifier 70 through bus 120 using the following criteria:

$$G = 0.9 \, V_s/V_{max} \quad (13)$$

where G is amplifier gain, Vs is saturation voltage of the amplifier, $V_{max}$ is maximum voltage of the absorption curve.

The first phase is repeated again, but with the gain of the amplifier 70 set correspondingly to criteria (13). In order to calculate the parameters a, b, c, m, n from the absorption curve as shown in FIG. 6, the device finds the $t_{max}$ which is time from beginning of the absorption curve (point D) to the maximum of the absorption voltage ($V_{max}$), and $t_{inf}$ (inflection point time).

Figure 6:
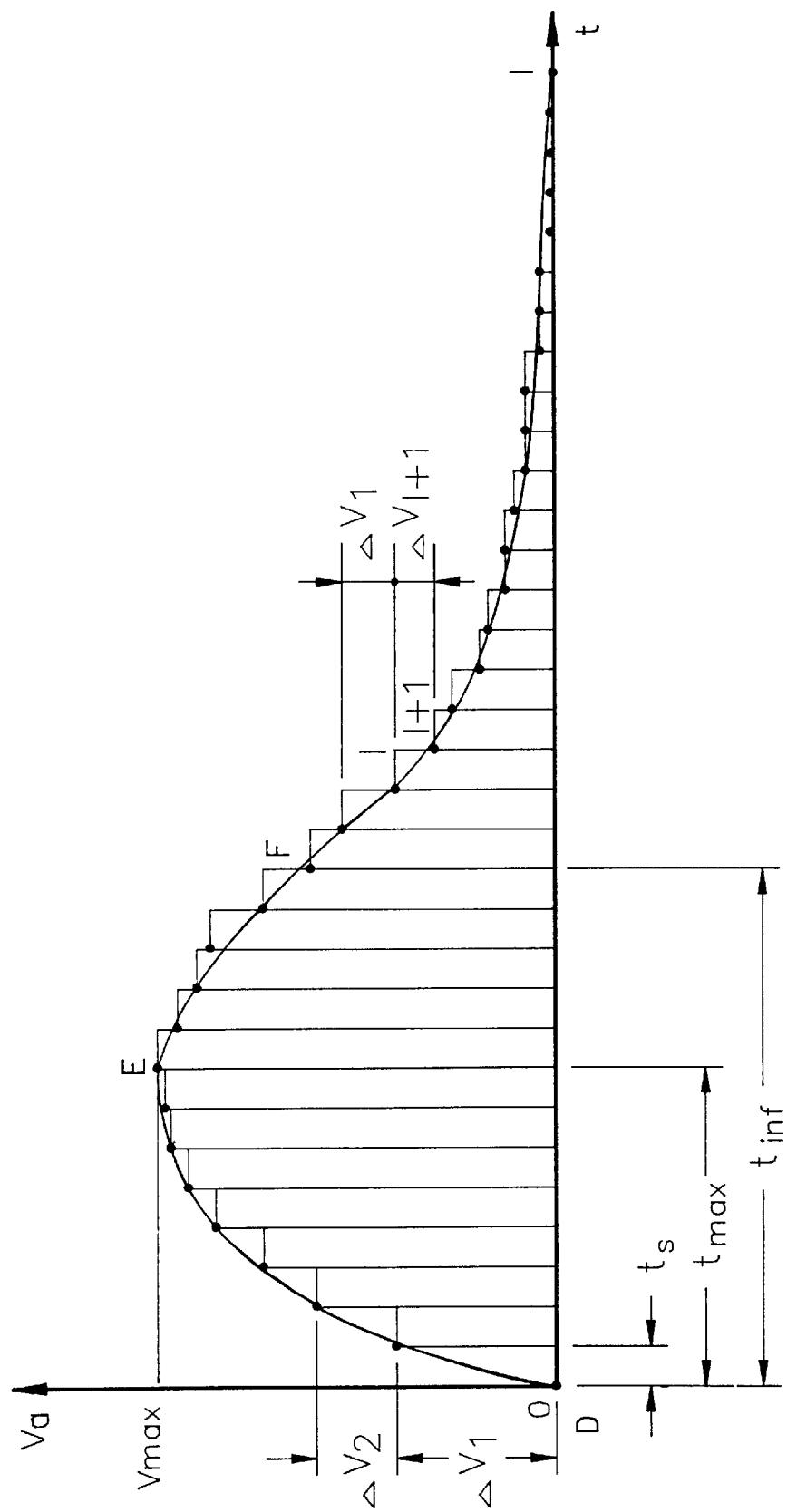
FIG. 6 is an exemplary dielectric absorption curve.

Assume that absorption curve of FIG. 6 consists of I points which are measured every sample time interval ($t_s$). MCU 90 calculates first derivatives in each point 0, 1, 2, 3 ... i, i+1 ... I, then finds the minimal value of the first derivative using the following criteria:

$$V'_k = |\Delta V_k/t_s| = \min \quad (14)$$

where $V'_k$ is first derivative; $\Delta V_k = V_i - V_{i+1}$; $V_i$ is voltage in point i; $V_{i+1}$ is voltage in point (i+1); $t_s$ is the sample time interval; k=1,2,3 ... I-1.

When the minimum of the first derivatives is found, the following expression defines $t_{max}$:

$$t_{max} = t_s k. \quad (15)$$

From $t_{max}$ MCU 90 calculates the parameter c:

$$c = 1/t_{max}. \quad (16)$$

The inflection point of the absorption curve DEFI is point where the second derivative of the absorption curve is equal zero. The second derivative may be found from:

$$V''_n = |(V'_k - V'_{k+1})/t_s^2| = \min \quad (17)$$

where $V''_n$ is second derivative; $V'_k$ is first derivative in the point; $V'_{k+1}$ is first derivative in (k+1) point; $t_s$ is the sample time interval; n=1, 2, 3 ... I-2. When the minimum of the second derivatives is found, the following expression defines $t_{inf}$:

$$t_{inf} = t_s n. \quad (18)$$

The MCU 90 calculates parameter b from the following expression:

$$b_{1,2} = -(2ct_{inf} + 1)/2 \pm (\sqrt{4ct_{inf} + 1})/2. \quad (19)$$

From (19) we have two values of the parameter b, using the following criteria MCU 90 selects one value of b:

$$0 < b < 1. \quad (20)$$

Furthermore, the MCU 90 calculates parameter a:

$$a = V_{max}/e \, t_{max}^b \quad (21)$$

where $V_{max}$ is the maximum value of the absorption curve, e=2.718.

The next step is the calculation of parameters m and n from the dielectric response function. The proposed device measures voltage on the FI interval of FIG. 3. This voltage is proportional to the decay current in dielectric of equation (10) if the amplifier 70 has constant input impedance. The decay current is proportional to the dielectric response function and may be written from (11):

$$i(t)Z = \begin{Bmatrix} K_1 Z & t^{-n} \\ K_2 Z & t^{-(m+1)} \end{Bmatrix} \quad (22)$$

where Z is impedance of the amplifier 70, $K_1$ and $K_2$ are constants. If Z is constant, then:

$$V(t) = \begin{Bmatrix} C_1 & t^{-n} \\ C_2 & t^{-(m+1)} \end{Bmatrix} \quad (23)$$

Where V(t)=i(t) Z, $C_1 = K_1 Z$, and $C_2 = K_2 Z$. The MCU 90 produces the decimal logarithm of the V(t) from (23):

$$\log_{10} V(t) = \begin{Bmatrix} \log_{10} C_1 - n\log_{10} t \\ \log_{10} C_2 - (m+1)\log_{10} t \end{Bmatrix}. \quad (24)$$

Figure 7:
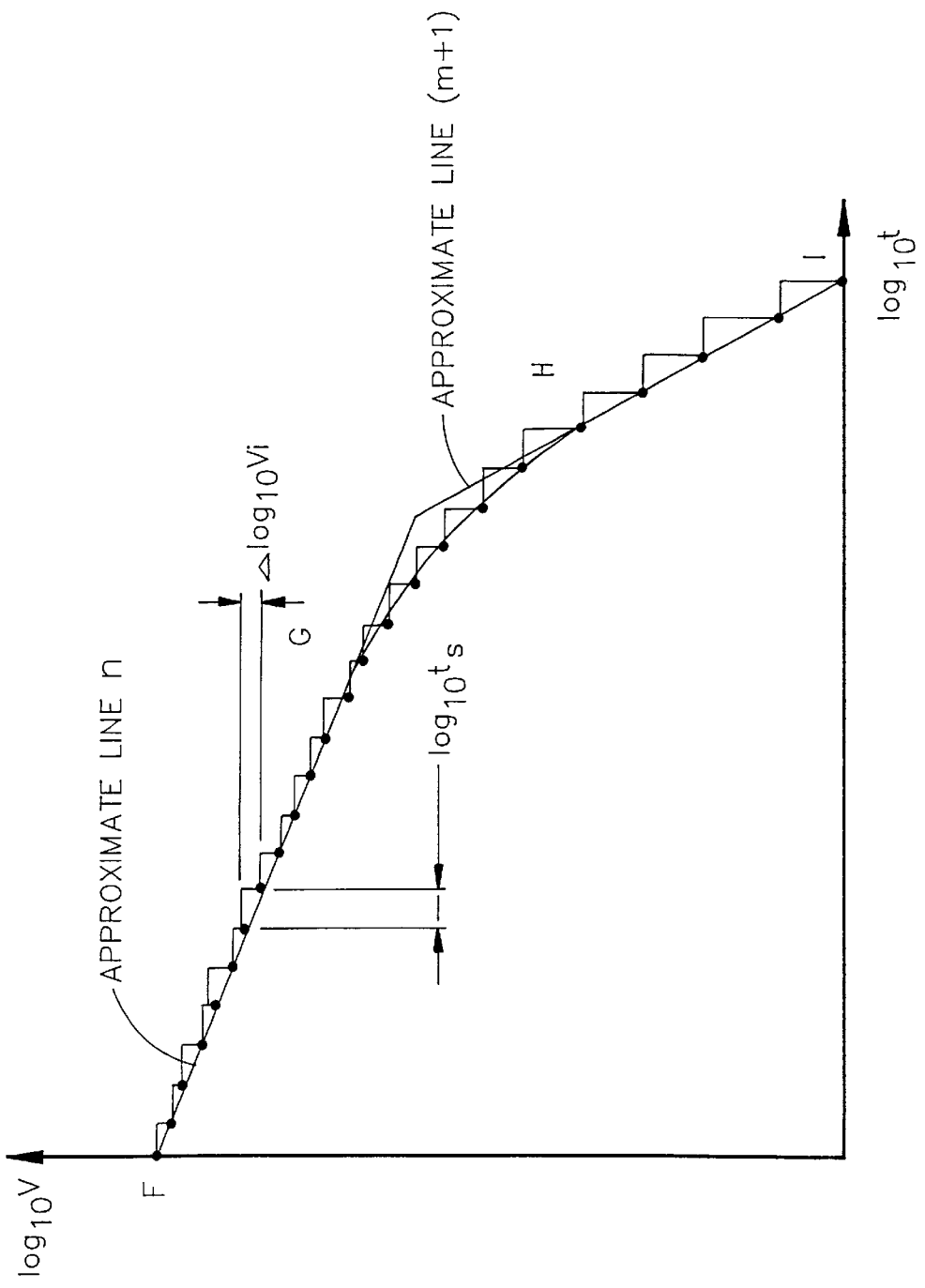
FIG. 7 is an exemplary dielectric response function.
Figure 8A:
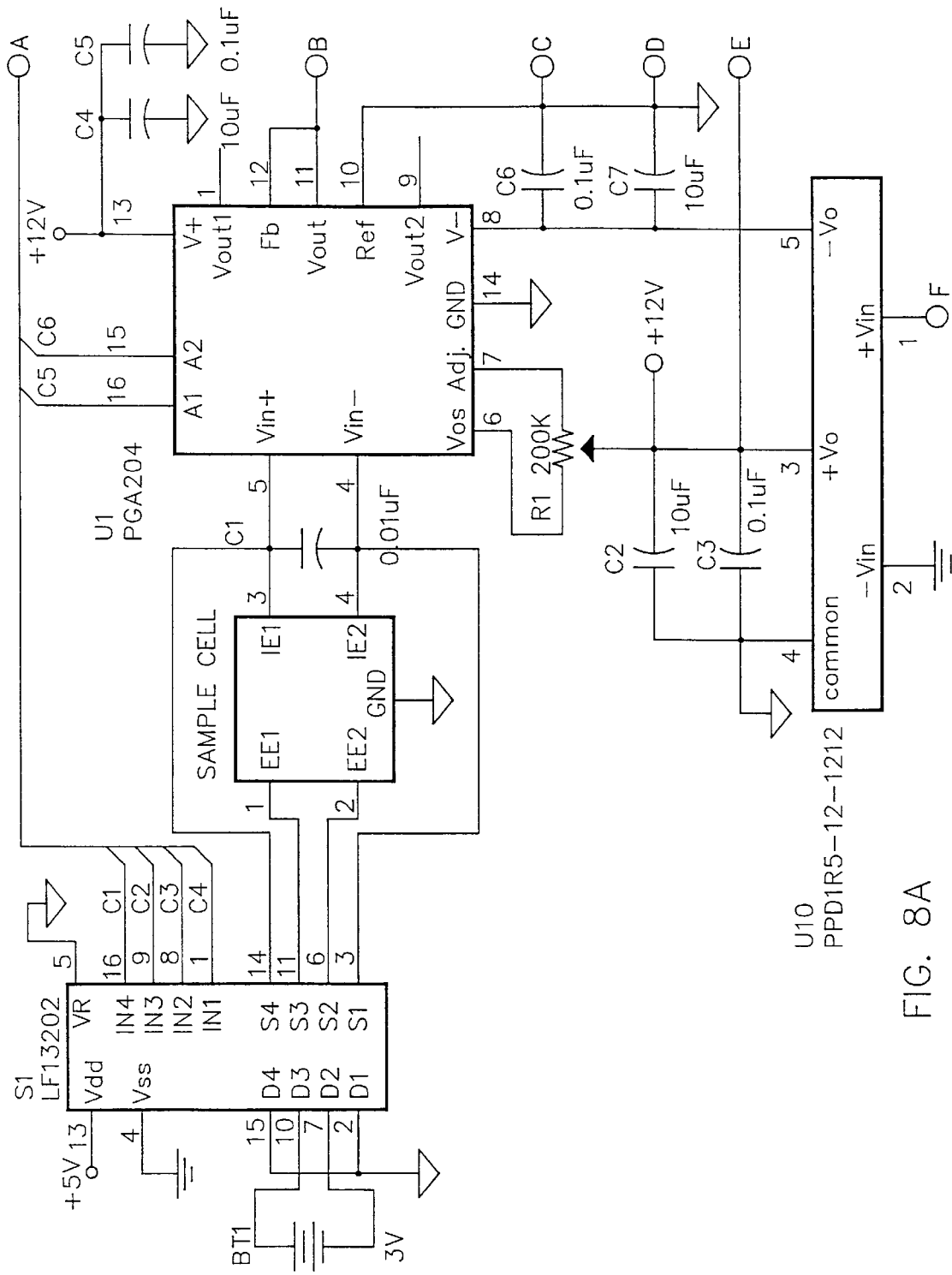
FIGS. 8A through 8E are an exemplary electrical scheme of a preferred embodiment of the instant invention.
Figure 8B:
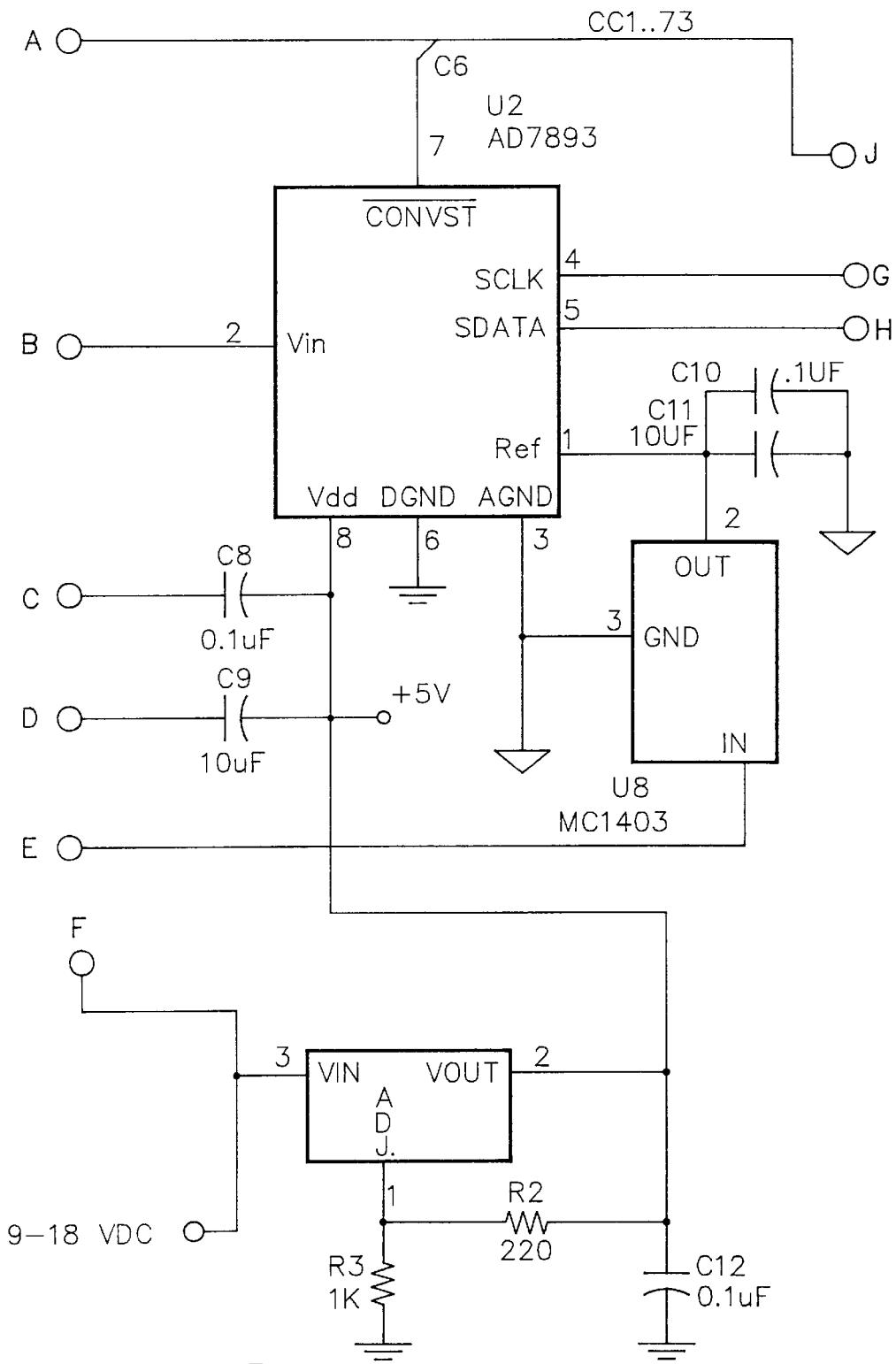
Figure 8C:
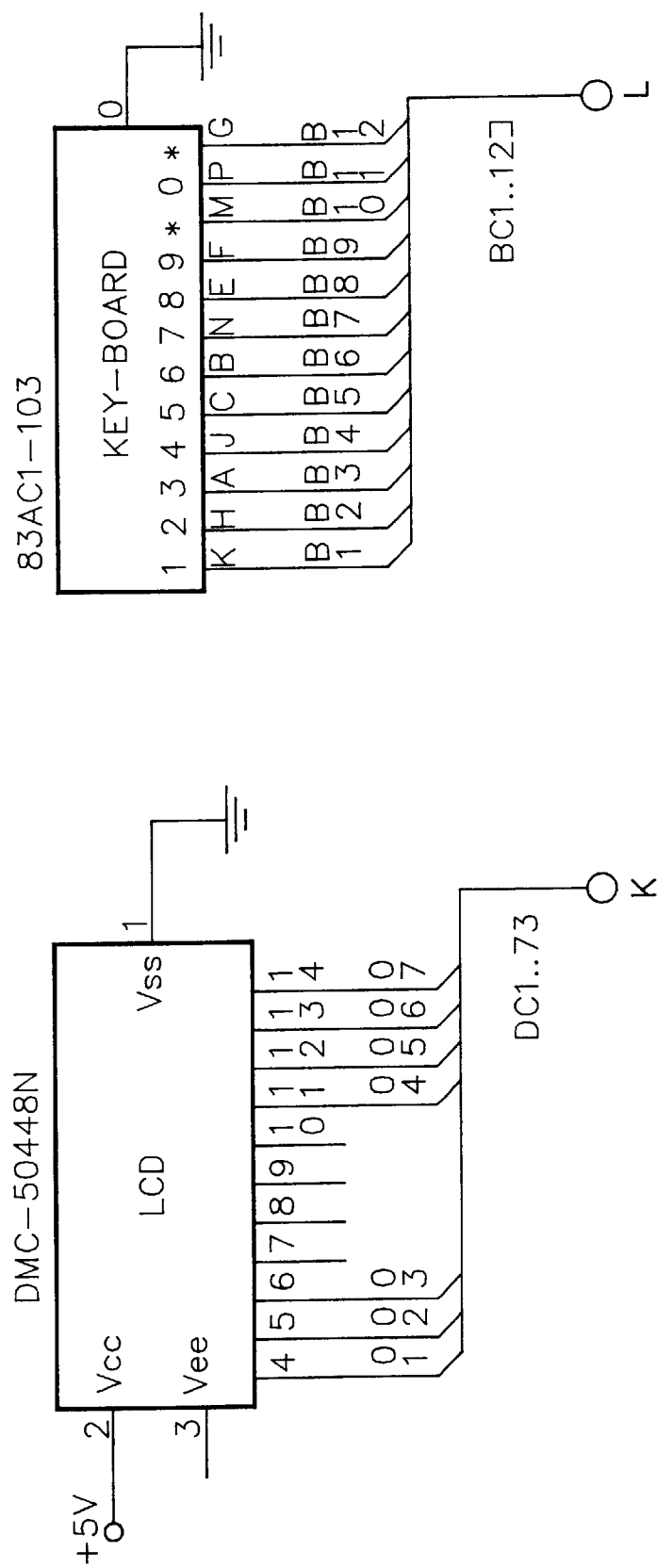
Figure 8D:
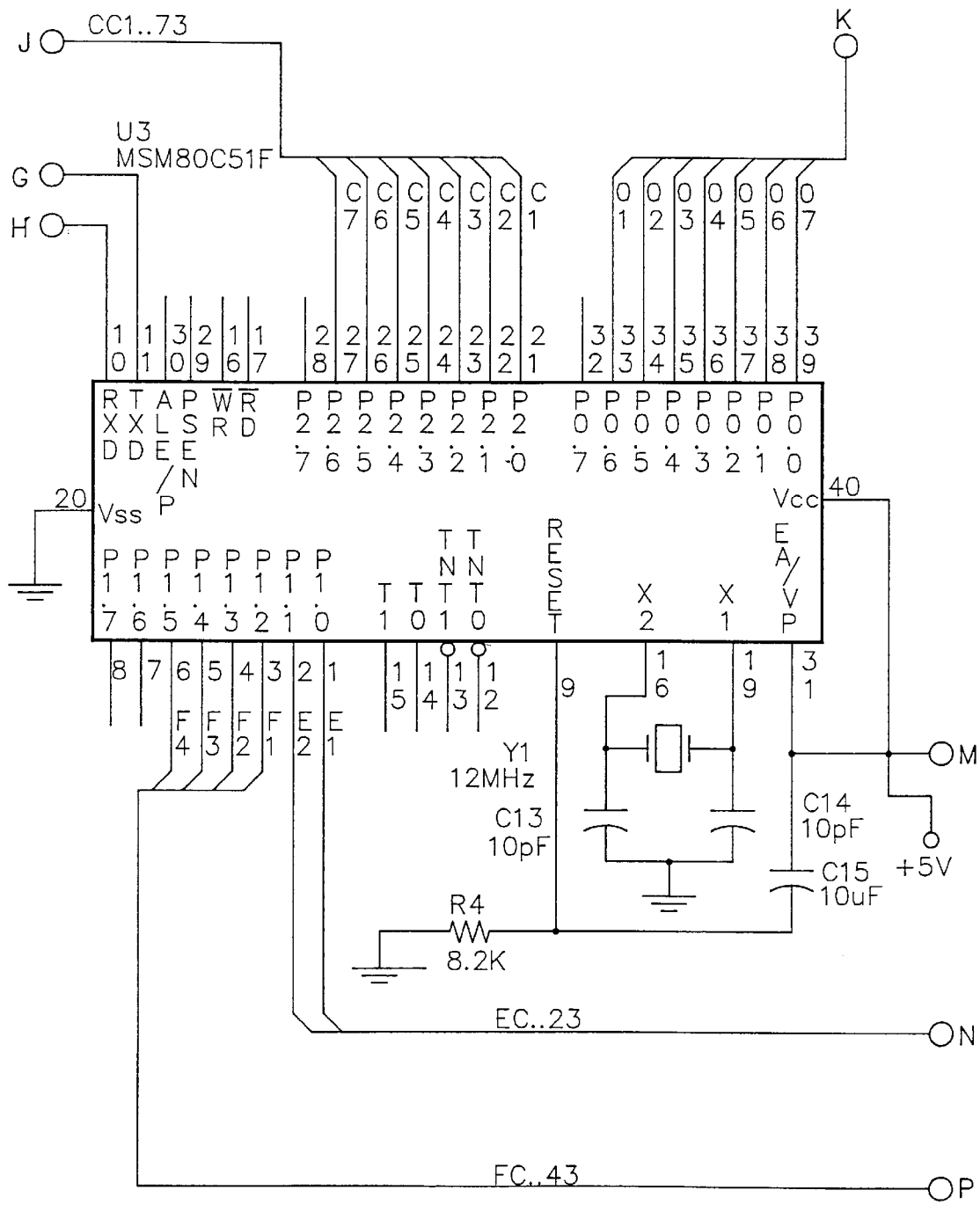
Figure 8E:
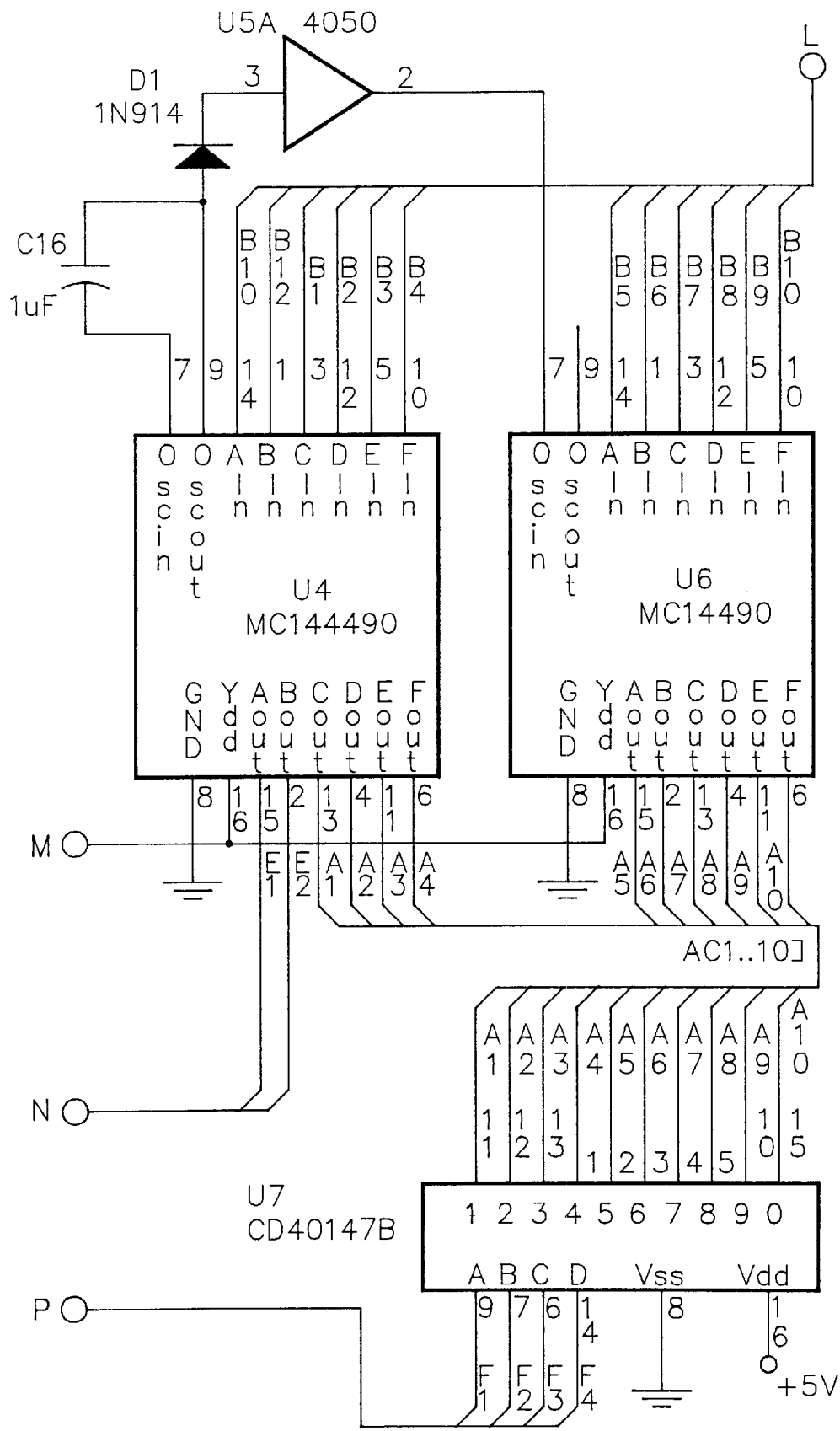
Figure 9A:
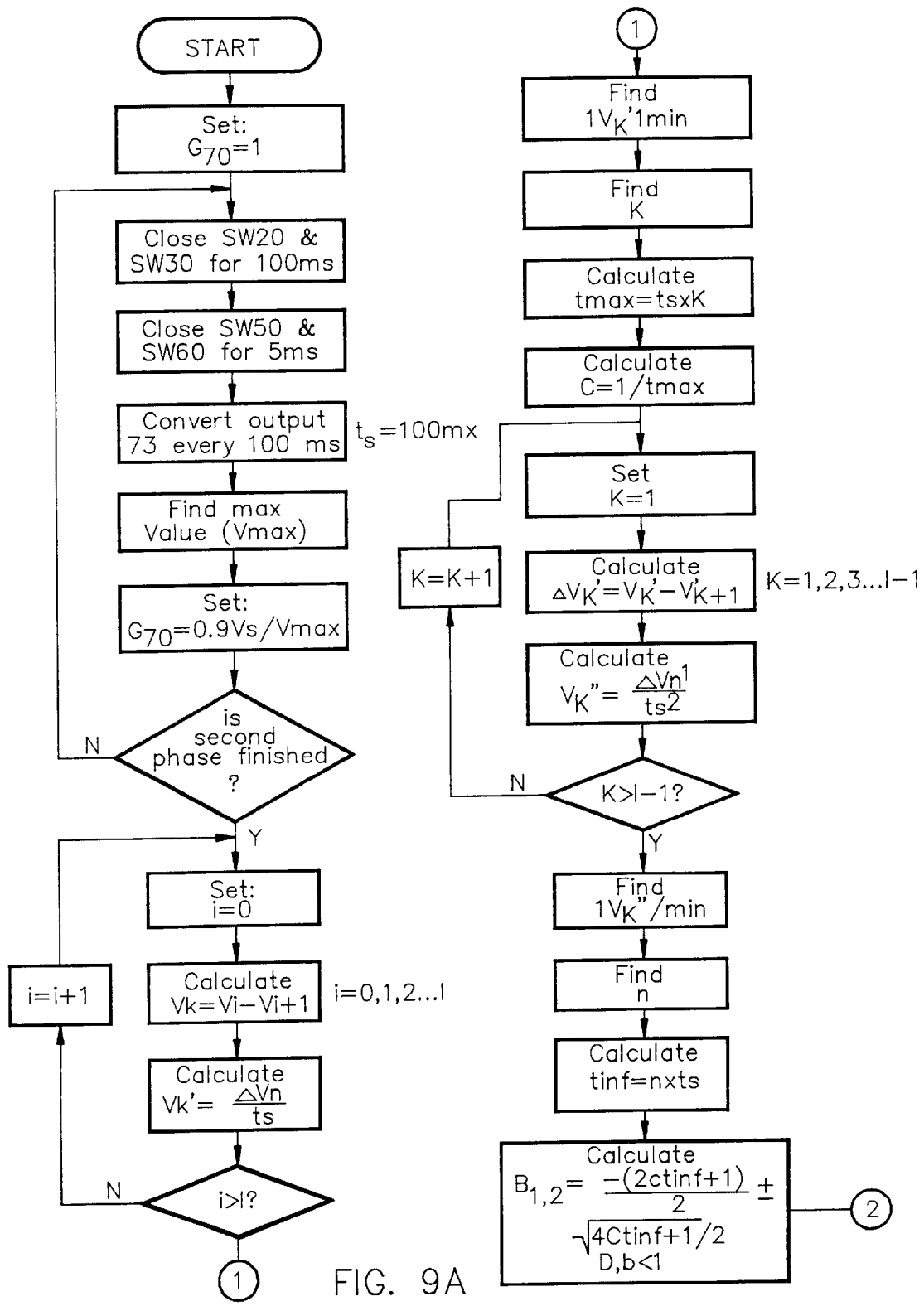
FIGS. 9A and 9B are flow diagrams of an exemplary process for determining time-domain dielectric spectroscopy.
Figure 9B:
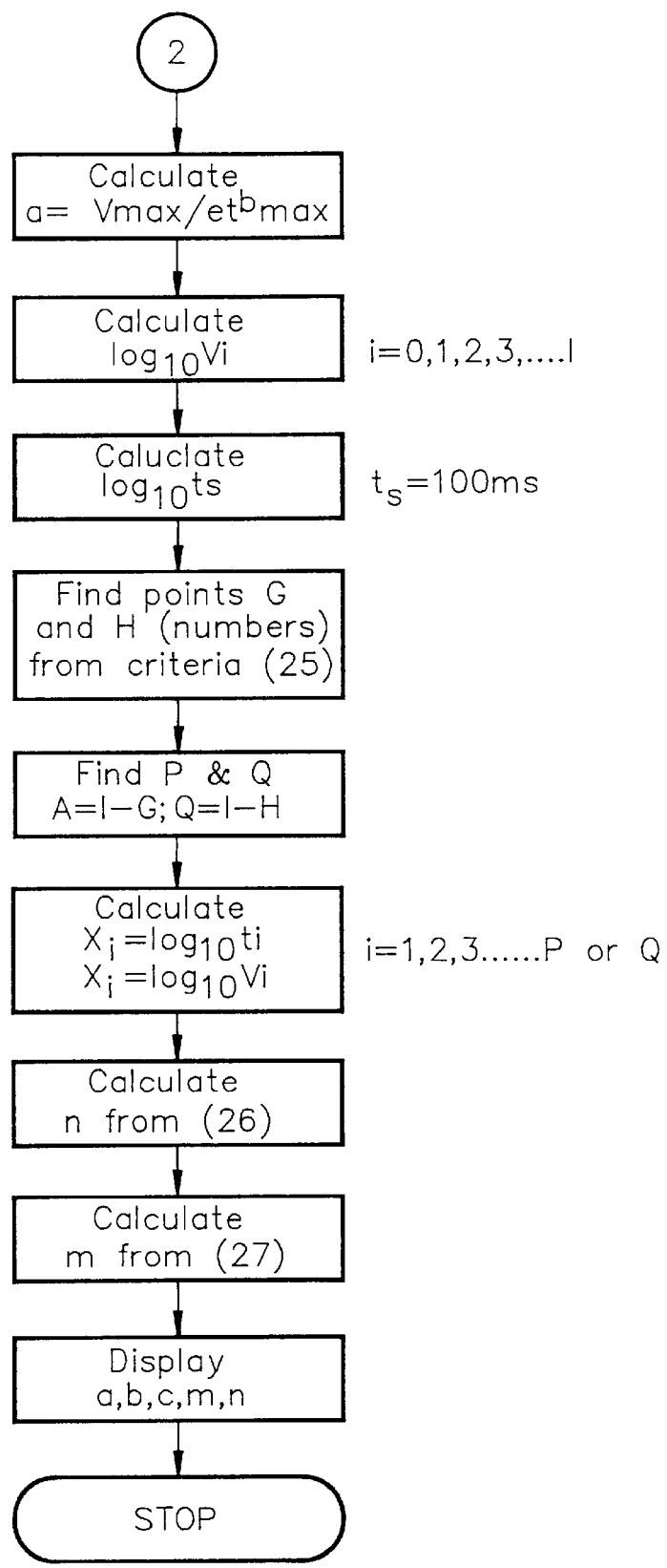

The graph of the dielectric response function is shown in FIG. 7. The FG and HI intervals may be approximated by two straight lines with slope coefficients n and (m+1) from (24). In real measurement we have the GH curve interval shown in FIG. 7. In order to decrease the approximation errors for FG and HI intervals shown in FIG. 7 MCU 90 leaves out all points which belong to the GH interval, and satisfy the next criteria:

$$|(\Delta\log_{10} V_i - \Delta\log_{10} V_{i+1})/\log_{10} t_s| > 2 \, e_n \, G \quad (25)$$

where i is previous the point and (i+1) of next point, i=1, 2, 3 ... I, where I is the total number of the points that belong to the dielectric response function of FIG. 7, $e_n$ is the noise of the amplifier 70, G is the gain of the amplifier 70. The n and m parameters (slope coefficients) may be found by MCU 90 using the following expression:

$$n = (P[X\,Y] - [X][Y])/(P[Y^2] - ([Y])^2) \quad (26)$$

$$m = (Q[X\,Y] - [X][Y])/(Q[Y^2] - ([Y])^2) \quad (27)$$

where P and Q are the numbers of points that belong to the FG and HI intervals shown in FIG. 7 respectively and where:

$$[XY] = \sum_{i=1}^{P;Q} X_i Y_i; \quad [Y] = \sum_{i=1}^{P;Q} Y_i; \quad [X] = \sum_{i=1}^{P;Q} X_i; \quad [Y^2] = \sum_{i=1}^{P;Q} Y_i^2;$$

where and $$X_i = \log_{10} t_i; \quad Y_i = \log_{10} V_i; \quad i = 1, 2, 3 \ldots Q \text{ or } P,$$

and where the description (P;Q) in the summation symbol means to use P for (26) and Q for (27).

Finally, MCU 90 had found all parameters: a, b, c, m, n which are the unique characteristics of dielectric.

The electrical principal scheme of the preferred embodiment is shown in FIGS. 8A–8E. Suitable components for constructing the apparatus are set forth in Table 1 below:

TABLE 1

| COMPONENT LOCATION | DESCRIPTION | SOURCE |
|---|---|---|
| S1 | Quad SPST Switches LF13202 | National Semiconductor |
| U1 | Programmable Gain Instrumentation Amplifier PGA204 | Burr-Brown |
| U2 | Analog-To-Digital Converter AD7893 | Analog Device |
| U3 | Microcontroller Unit MSM80C51F | OKI |
| U4, U6 | Hex Contact Bounce Eliminator MC14490 | Motorola |
| U5 | Hex Non-Interfering Buffer MC14050 | Motorola |
| U7 | 10 Line-to-4 Line BCD Priority Encoder CD40147B | Harris |
| U8 | Voltage Reference MC1403 | Motorola |
| U9 | Voltage Regulator LM317L | National Semiconductor |
| U10 | DC-to-DC Converter PPD1R5-12-1212 | Lambda |
|  | LCD, DMC-50448N | Optrex |
|  | Keyboard, 83AC1-103 | Grayhill |
| BT1 | Battery, CR2025 | Panasonic |
| R1 | Potentiometer, Series 3266, 200K | Bourns |
| R2 | Resistor, 220 Ohm ± 1%, ¼ W, Metal Film | Yageo |
| R3 | Resistor, 2K ± 1%, ¼ W, Metal Film | Yageo |
| R4 | Resistor, 8.2K ± 5%, ¼ W, Carbon Film | Yageo |
| C1 | Capacitor, 0.01 uF, 16 V, Polyester | Panasonic |
| C2, C4, C7, C9, C11, C15 | Capacitor, 10 uF, 50 V, Tantalum | Panasonic |
| C3, C5, C6, C8, C10, C12 | Capacitor, 0.1 uF, 50 V, Ceramic Disc | Panasonic |
| C13, C14 | Capacitor, 10 pF, 50 V, Ceramic Disc | Panasonic |
| C16 | Capacitor, 1 uF, 63 V, Monolithic Ceramic | Panasonic |
| D1 | Diode, 1N914 | National Semiconductor |
| Y1 | Microprocessor Crystal, 12 MHz | CTS |

COMPARISON OF THE KNOWN ART WITH THE PRESENT INVENTION

Sanders' U.S. Pat. No. 5,461,321 describes the measurement of the value of a capacitance. Blackwell's U.S. Pat. No. 3,784,905 describes the measurement of a dielectric strength. Bungay's U.S. Pat. No. 4,429,272 describes the measurement of a change in the dielectric constant of a fluid. Ludlow's U.S. Pat. No. 3,753,092 describes the measurement of small changes in the dielectric constant of insulating liquids. Day's U.S. Pat. No. 4,777,431 describes the measurement of the dielectric properties of a material by applying time-varying voltage (e.g. an AC signal) to a dielectric material and measuring the amplitude of the current and its phase, relative to the input voltage. Capots' U.S. Pat. No. 4,433,286 describes the measurement of the conductance and capacitance of a material. Bechtel's U.S. Pat. No. 5,394,097 describes the measurement of the real and imaginary parts of permittivity in dielectric materials.

The present invention describes the measurement of the absorption function parameters a,b,c and the dielectric response function parameters m and n.

SUMMARY

Known art inventions are quite different from the present invention in that they measure the characteristics of the dielectric during charge/discharge cycle or under alternating current. Thus, the measurements take place on the OABC interval (FIG. 3) for the known art. The present invention, on the other hand, measures dielectric absorption and response function parameters on the DEFI interval (FIG. 3), and makes it possible to identify dielectrics more precisely than any other previously mentioned measurement known in the art.

Figure 10:
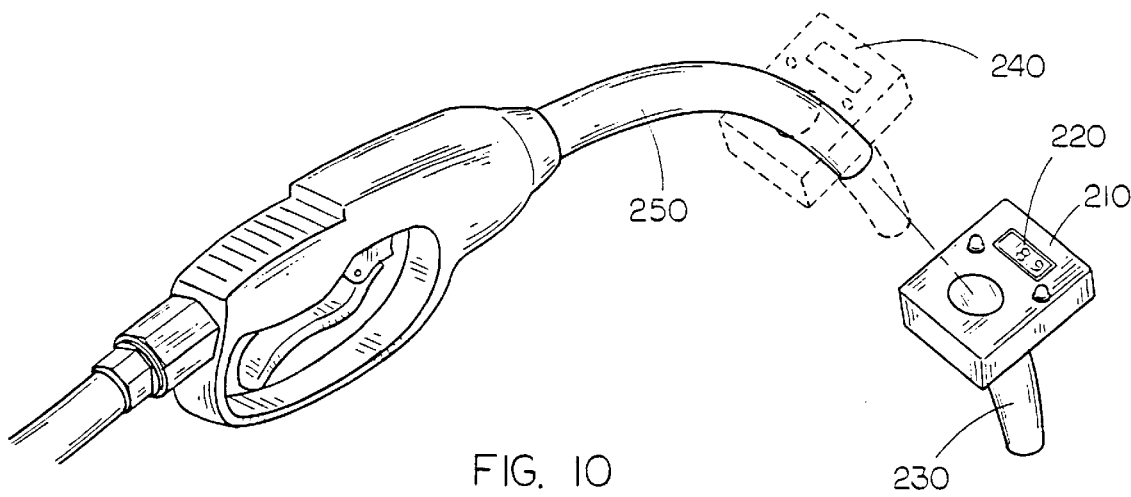
FIG. 10 illustrates an exemplary, portable TDS device for consumer use in monitoring fuel content by inserting a gas nozzle through the TDS device and thereby measuring fuel characteristics.
Figure 11:
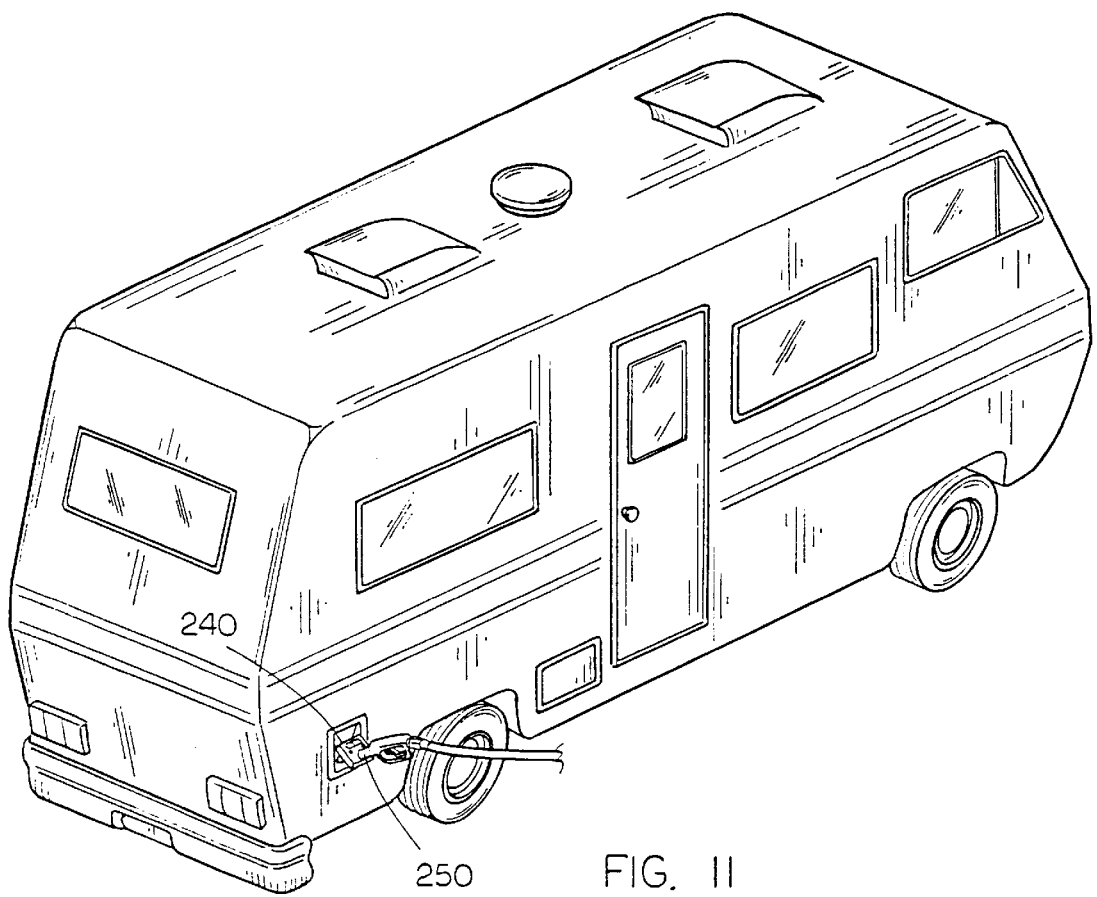
FIG. 11 demonstrates the device of FIG. 10 in use during refueling of a vehicle.
Figure 12:
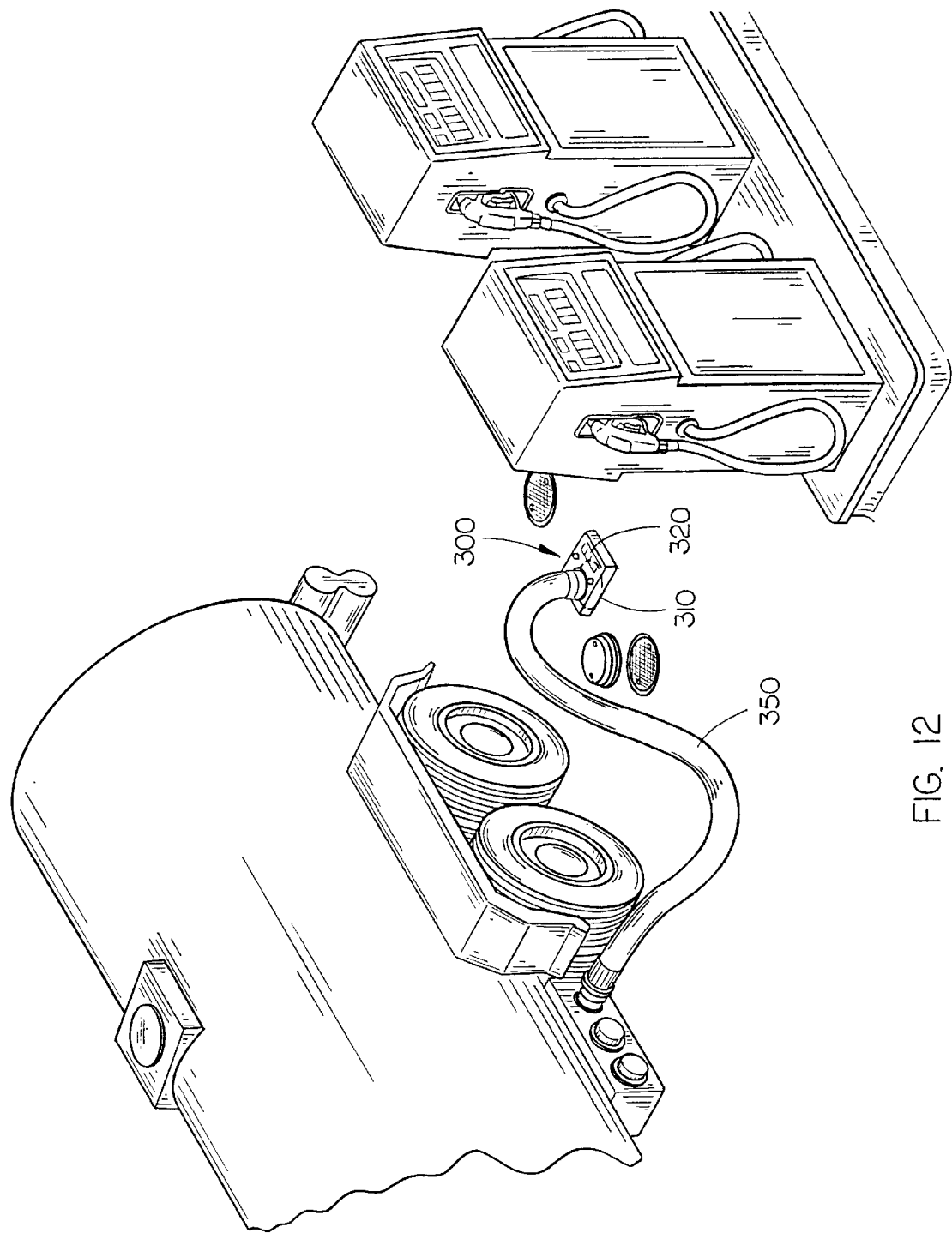
FIG. 12 illustrates an exemplary TDS device for retailer use in monitoring fuel content during delivery by a wholesaler to an underground holding tank.

Finally, two exemplary applications of the device are represented by FIGS. 10 through 12. In FIG. 10 the device represented 200 consists of a housing 210 with a display window 220. Transecting the housing is a cylinder 230 of sufficient size to accommodate the dispensing nozzle 250 of a typical gas station fuel dispenser.

A sample cell (see FIGS. 4 and 5) is disposed within the cylinder 230 so as to come in contact with the fuel as it is being dispensed into a vehicle or fuel receptacle through nozzle 250. All other components depicted in FIG. 4 are disposed within housing 210 such that display 100 (FIG. 5) is visible through display window 220. It is anticipated that this device is programmed to assess octane levels and fuel purity with the display 100 registering octane levels. A consumer may use such a device when fueling a vehicle as shown in FIG. 11.

The more sophisticated device 300 represented in FIG. 12 consists of a somewhat larger housing 310 with a display window 320. Transecting the housing is a cylinder (not shown) of sufficient size to accommodate the dispensing nozzle 350 of a typical bulk fuel dispenser. A sample cell as shown in FIGS. 4 and 5 is disposed within the cylinder so as to come in contact with the fuel as it is being dispensed into a subterranean storage tank (not shown). All other components depicted in FIG. 4 are disposed within housing 310 such that display 100 FIG. 4 is visible through display window 320. It is anticipated that this device is programmed to assess octane levels and fuel purity with the display 100 registering a number of different parameters for the monitoring of fuel quality and content by retailers.

I claim:

1. An apparatus for measuring the absorption function and the dielectric response function parameters of a dielectric substance, comprising:
   (a) a charger for applying a voltage to a dielectric substance such that a stable charge is obtained in said dielectric substance;
   (b) a discharger for discharging said charge from said dielectric substance such that said charge applied by said charger is substantially discharged;
   (c) a sensor for measuring the absorption function and the dielectric response function parameters of a dielectric substance.

2. The apparatus of claim 1 wherein said charger charges said dielectric substance to its maximum charge holding capacity.

3. The apparatus of claim 2 wherein said charger holds said maximum charge in said dielectric substance for at least some period of time after said maximum charge is obtained in said dielectric substance.

4. The apparatus of claim 3 wherein said at least some period of time is at least 1 ms.

5. The apparatus of claim 3 wherein said at least some period of time is between 10 ms and 1 s.

6. An apparatus for identification of dielectric substances by utilization of time-domain dielectric spectroscopy, comprising:
   (a) a sample cell having at least first and second terminals, said sample cell being capable of sensing the dielectric properties of a dielectric substance accommodated by said sample cell, wherein said dielectric substance in combination with said sample cell electrically behave as a capacitor, the dielectric substance accommodated by said sample cell being the dielectric of said capacitor;

(b) an input voltage supply means operatively connected to said at least first and second terminals of said sample cell for applying an input voltage to said sample cell such that the capacitor formed by said sample cell and the dielectric substance to be identified exhibits the electrical behavior of a capacitor at the first and second terminals of said sample cell;

(c) a sensor connected to said at least first and second terminals of said sample cell, said sensor being responsive to the electrical behavior exhibited by the capacitor formed by said sample cell as a result of at least one charge/discharge cycle wherein said sensor measures the free relaxation of the dielectric substance after said at least one charge/discharge cycles.

7. The apparatus of claim 6 wherein said input voltage supply means comprises a direct voltage source and at least one normally open switch.

8. The apparatus of claim 6 wherein said sensor is operatively connected to said input voltage supply means for providing control thereof.

9. The apparatus of claim 7 wherein said sensor provides selective control of the opening and closing of said at least one normally open switch.

10. The apparatus of claim 6 wherein said sensor comprises:

(a) a low noise amplifier for providing an amplified output signal in response to an input signal appearing at the first and second terminals of said sensor, the input signal being the electrical behavior exhibited by the capacitor formed by said sample cell and the dielectric substance to be identified;

(b) an analog-to-digital converter receiving the amplified output signal of said low noise amplifier for providing a binary-coded digital signal proportional to the amplified output of said low noise amplifier; and (c) a microprocessor means receiving the binary-coded digital signal of said analog-to-digital converter, said microprocessor being capable of processing the electrical behavior exhibited by the capacitor formed by said sample cell and the dielectric substance to be identified such that the dielectric substance to be identified may be thereby identified.

11. The apparatus of claim 7 wherein said at least one normally open switch is at least two switches wherein one of said at least two switches is a charge switch and at least one of said at least two switches is a discharge switch.

12. The apparatus of claim 10 wherein said low noise amplifier has a noise figure of less than 0.5 decibels in the frequency band ranging from 0 hertz to 1 megahertz.

13. The apparatus of claim 10 wherein the binary-coded digital signal of said analog-to-digital converter is a 12 bit binary-coded digital signal.

14. The apparatus of claim 10 wherein said analog-to-digital converter has a conversion time less than or equal to 10 microseconds.

15. The apparatus of claim 10 wherein said microprocessor means includes 8 bit input ports.

16. The apparatus of claim 10 wherein said microprocessor means is driven with a clock frequency of at least 10 megahertz.

17. The apparatus of claim 6 wherein said the capacitor formed by said sample cell and said dielectric substance to be identified has a capacitance of at least 100 picofarads when the dielectric substance is air.

18. The apparatus of claim 6 wherein said the capacitor formed by said sample cell and said dielectric substance to be identified has a Q factor of at least 1000 at 10 megahertz.

19. A method for identification of dielectric substances by utilization of time-domain dielectric spectroscopy, comprising:

(a) charging a dielectric substance such that a stable charge is obtained in said dielectric substance;

(b) discharging said charge from said dielectric substance; and (c) measuring at least one of the absorption function and the dielectric response function parameters of said dielectric substance after said charge/discharge cycle of said dielectric substance.

20. A method for identification of dielectric substances by utilization of time-domain dielectric spectroscopy, comprising:

(a) applying a sensor to the dielectric substance to be identified wherein the dielectric substance in combination with the sensor integrate to thereby form and electrically behave as a capacitor, the dielectric substance to be identified being the dielectric of the capacitor;

(b) measuring the electrical behavior of the capacitor formed by the integrated combination of the sensor and the dielectric substance to be identified;

(c) calculating the dielectric response function parameters and the dielectric absorption parameters of the dielectric substance to be identified; and (d) identifying the dielectric substance to be identified by comparing the calculated dielectric response function parameters and the dielectric absorption parameters of the dielectric substance to be identified with known dielectric response function parameters and dielectric absorption parameters of known dielectric substances.

21. The method according to claim 20 wherein said measuring step includes measuring the absorption and dielectric response function of the dielectric substance to be identified.

22. The method according to claim 20 wherein said measuring step includes measuring the absorption voltage of the dielectric substance to be identified.

23. The method according to claim 20 wherein said calculating step includes filtration of the measured discharge voltages.

24. The method according to claim 20 wherein said calculating step includes identifying points which belong to approximated lines representing the electrical behavior of the dielectric substance to be identified.

25. The method according to claim 20 wherein said calculating step includes calculating slope coefficients of approximated lines representing the electrical behavior of the dielectric substance to be identified.

26. The method according to claim 20 wherein said calculating step includes approximating the absorption curve of the dielectric substance to be identified.

27. The method of claim 20 wherein the known dielectric absorption function and dielectric response function of at least one known dielectric substance is stored in electronic memory.

* * * * *